Figure 1:
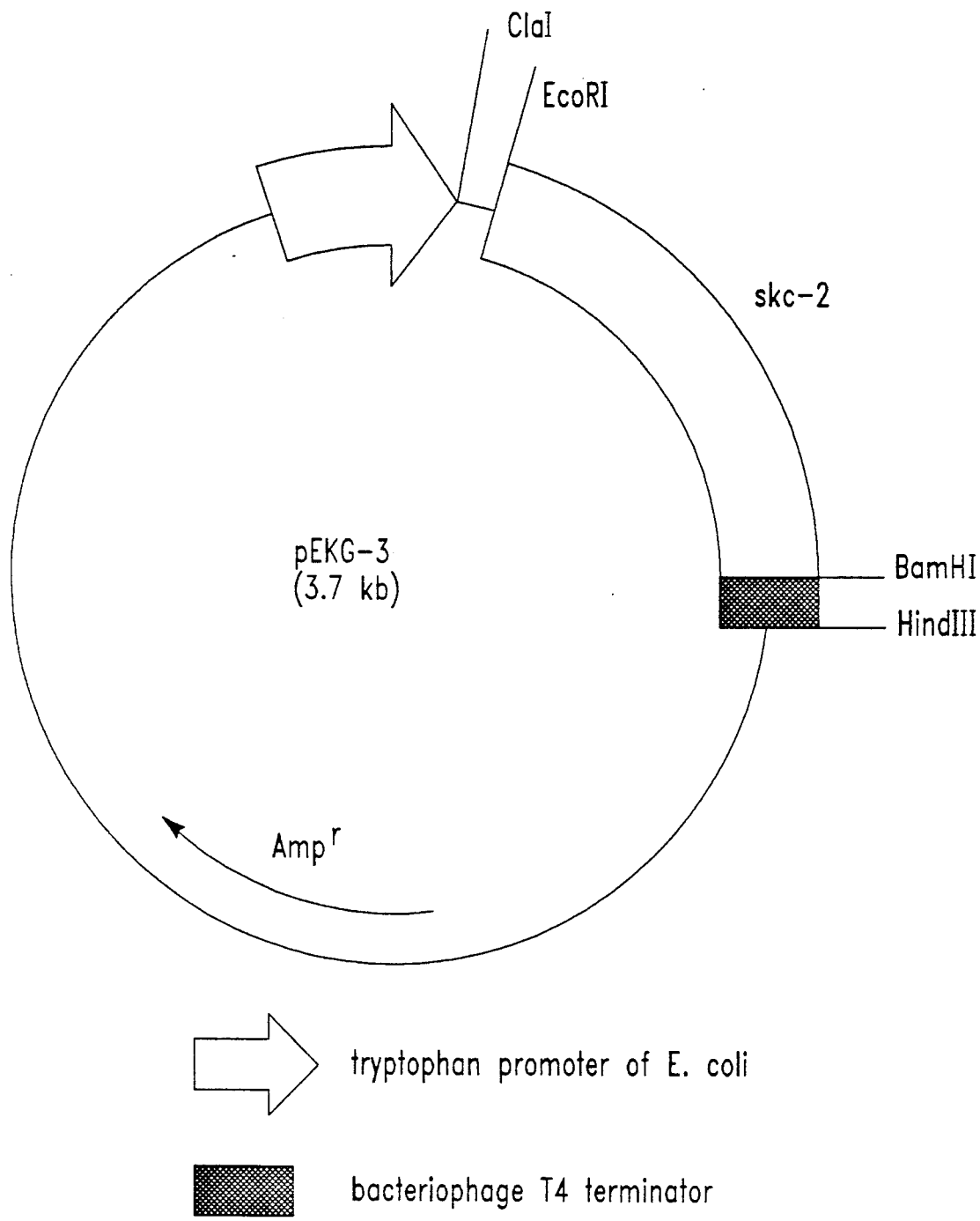

United States Patent [19]
Garcia et al.

[11] Patent Number: 5,296,366
[45] Date of Patent: Mar. 22, 1994

[54] METHOD FOR THE ISOLATION AND EXPRESSION OF A GENE WHICH CODES FOR STREPTOKINASE, NUCLEOTIDE SEQUENCE OBTAINED, RECOMBINANT DNA AND TRANSFORMED MICROORGNAISMS

[75] Inventors: Mario P. E. Garcia; Aimee P. Felipe; Roger R. Chaplen; Ricardo S. Doce; Luciano F. H. Marrero, all of Havana; Pedro R. Collazo, Artemisa; Anaisel C. Ramirez, Havana; Emilio A. M. Munoz, Ciego de Avila; Walfrido B. Martinez, Havana; Magalys C. Somavilla, Havana; Alicia P. Fernandez, Havana; Jose d. d. Garcia, Havana; Luis S. H. Martinez Havana, all of Cuba

[73] Assignee: Centro de Ingenieria Genetica y Biotecnologia, Cuba

[21] Appl. No.: 703,778

[22] Filed: May 22, 1991

[30] Foreign Application Priority Data

May 23, 1990 [CU] Cuba ............................. 90/90

[51] Int. Cl.$^5$ ............... C12N 15/58; C12N 15/70; C12N 15/81
[52] U.S. Cl. ................. 435/216; 435/69.1; 435/69.8; 435/71.1; 435/71.2; 435/172.3; 435/252.3; 435/252.33; 435/320.1; 435/254.2; 435/254.23; 536/23.2
[58] Field of Search ............. 536/27, 23.2; 435/69.1, 435/69.8, 71.1, 71.2, 172.3, 216, 252.3, 255, 252.33, 320.1

[56] References Cited
PUBLICATIONS

Hagenson, M. J. et al. "Expression of Streptokinase in *Pichia pastoris* Yeast" Enzyme. Microb. Technol. 11: 650–656 (Oct. 1989).

S. K. Park et al. "The Leader Sequence of Streptokinase . . . " Biochem. Biophys. Res. Commun. 174(1) 282–286 (Jan. 1991).

*Primary Examiner*—Robert A. Wax
*Assistant Examiner*—Rebecca Prouty
*Attorney, Agent, or Firm*—Peter L. Michaelson; Edward M. Fink

[57] ABSTRACT

The present invention relates to the field of biotechnology and genetic engineering and in particular a novel nucleotide sequence which codes for a streptokinase, as well as the recombinant DNA obtained therefrom which is used for the transformation of various host organisms.

The present invention is based on the isolation of a new gene which codes for streptokinase from *Streptococcus equisimilis* of type C (strain ATCC-9542) and the cloning and expression thereof in prokaryotic (*E. coli*) and eukaryotic (*Pichia pastoris*) hosts, for which it includes the vehicles of expression which contain the genetic sequences of said gene, as well as the microorganisms transformed with these vectors capable of producing streptokinase.

The protein obtained thereby can be used in clinical medicine as a therapeutic agent, in the treatment of disorders such as thromboembolic obstructions including coronary thrombosis.

26 Claims, 3 Drawing Sheets

```
SKC-2  MIAGPEWLLDRPSVNNSQLVVSVAGTVEGTNQDISLKFFEIDLTSRPAHGGKTEQGLSPKSKPFATDSG
SKC    ..................................................................
SKG    ......Y...........................................L...............
SKA    ..................................................E..............K.

SKC-2  AMPHKLEKADLLKAIQEQLIANVHSNDDYFEVIDFASDATITDRNGKVYFADKDGSVTLPTQPVQEFLL
SKC    ...S..............................................................
SKG    ...S..........................................................I...
SKA    .............................G...............D....................

SKC-2  SGHVRVRPYKEKPIQNQAKSVDVEYTVQFTPLNPDDDFRPGLKDTKLLKTLAIGDTITSQELLAQAQSI
SKC    ..................................A...............................
SKG    .....K..QP.AVH.S.ER.N.N.E.S.VSETG.L..T.L.RNQYH.T...V..SLS....A.I..F.
SKA    ..................................................................

SKC-2  LNKTHPGYTIYERDSSIVTHDNDIFRTILPMDQEFTYHVKNREQAYEINKKSGLNEEINNTDLISEKYY
SKC    ....N..............................................R...R...........
SKG    ..S.K..D.IITK......................I.D....KA.S.T.IE.KT.............
SKA    ..................................................................

SKC-2  VLKKGEKPYDPFDRSHLKLFTIKYVDUNTNELLKSEQLLTASERNLDFRDLYDPRDKAKLLYNNLDAFG
SKC    ...................................D...............................
SKA    ..................................N...K...........................

SKC-2  IMDYTLTGKVEDNHDDTNRIITVYMGKRPEGENASYHLAYDKDRYTEEEREVYSYLRYTGTPIPDNPNDK
SKC    ..................................................................
SKG    ..................................................................
SKA    .................................................................K.
```

FIG. 2

SEQUENCE LISTING ( 1 ) GENERAL INFORMATION:

( i i i ) NUMBER OF SEQUENCES:14

( 2 ) INFORMATION FOR SEQ ID NO: 1:

( i ) SEQUENCE CHARACTERISTICS:
        ( A ) LENGTH:1245 base pairs
        ( B ) TYPE:Nucleotide with corresponding protein
        ( C ) STRANDEDNESS:single
        ( D ) TOPOLOGY:linear ( i i ) MOLECULE TYPE:genomic DNA ( v i ) ORIGINAL SOURCE:
        ( A ) ORGANISM:Streptococcus equisimilis from group C of Lanfield definition ( v i i ) IMMEDIATE SOURCE:ATCC-9542 strain ( i x ) FEATURE:from 1 to 1245 bp mature peptide
        ( D ) OTHER INFORMATION:
            Properties: Streptokinase gene
            The gene product binds to human plasminogen
            The gene product is an activator of human plasminogen ( x i ) SEQUENCE DESCRIPTION: SEQ ID NO:1:

```
ATT  GCT  GGA  CCT  GAG  TGG  CTG  CTA  GAC  CGT  CCA  TCT  GTC  AAC  AAC  AGC    4 8
Ile  Ala  Gly  Pro  Glu  Trp  Leu  Leu  Asp  Arg  Pro  Ser  Val  Asn  Asn  Ser
 1             5                        10                       15

CAA  TTA  GTT  GTT  AGC  GTT  GCT  GGT  ACT  GTT  GAG  GGG  ACG  AAT  CAA  GAC    9 6
Gln  Leu  Val  Val  Ser  Val  Ala  Gly  Thr  Val  Glu  Gly  Thr  Asn  Gln  Asp
          20                       25                       30
```

| | | | | | | | | | | | | | | | | |
|---|---|---|---|---|---|---|---|---|---|---|---|---|---|---|---|---|
| ATT | AGT | CTT | AAA | TTT | TTT | GAA | ATT | GAC | CTA | ACA | TCA | CGA | CCT | GCT | CAT | 144 |
| Ile | Ser | Leu | Lys | Phe | Phe | Glu | Ile | Asp | Leu | Thr | Ser | Arg | Pro | Ala | His | |
| | | 35 | | | | | 40 | | | | | 45 | | | | |
| GGA | GGA | AAG | ACA | GAG | CAA | GGC | TTA | AGT | CCA | AAA | TCA | AAA | CCA | TTT | GCT | 192 |
| Gly | Gly | Lys | Thr | Glu | Gln | Gly | Leu | Ser | Pro | Lys | Ser | Lys | Pro | Phe | Ala | |
| | 50 | | | | | 55 | | | | | 60 | | | | | |
| ACT | GAT | AGT | GGC | GCG | ATG | CCA | CAT | AAA | CTT | GAA | AAA | GCT | GAC | TTA | CTA | 240 |
| Thr | Asp | Ser | Gly | Ala | Met | Pro | His | Lys | Leu | Glu | Lys | Ala | Asp | Leu | Leu | |
| 65 | | | | | 70 | | | | | 75 | | | | | 80 | |
| AAG | GCT | ATT | CAA | GAA | CAA | TTG | ATC | GCT | AAC | GTC | CAC | AGT | AAC | GAC | GAC | 288 |
| Lys | Ala | Ile | Gln | Glu | Gln | Leu | Ile | Ala | Asn | Val | His | Ser | Asn | Asp | Asp | |
| | | | | 85 | | | | | 90 | | | | | 95 | | |
| TAC | TTT | GAG | GTC | ATT | GAT | TTT | GCA | AGC | GAT | GCA | ACC | ATT | ACT | GAT | CGA | 336 |
| Tyr | Phe | Glu | Val | Ile | Asp | Phe | Ala | Ser | Asp | Ala | Thr | Ile | Thr | Asp | Arg | |
| | | | 100 | | | | | 105 | | | | | 110 | | | |
| AAC | GGC | AAG | GTC | TAC | TTT | GCT | GAC | AAA | GAT | GGT | TCG | GTA | ACC | TTG | CCG | 384 |
| Asn | Gly | Lys | Val | Tyr | Phe | Ala | Asp | Lys | Asp | Gly | Ser | Val | Thr | Leu | Pro | |
| | | 115 | | | | | 120 | | | | | 125 | | | | |
| ACC | CAA | CCT | GTC | CAA | GAA | TTT | TTG | CTA | AGC | GGA | CAT | GTG | CGC | GTT | AGA | 432 |
| Thr | Gln | Pro | Val | Gln | Glu | Phe | Leu | Leu | Ser | Gly | His | Val | Arg | Val | Arg | |
| | 130 | | | | | 135 | | | | | 140 | | | | | |
| CCA | TAT | AAA | GAA | AAA | CCA | ATA | CAA | AAT | CAA | GCG | AAA | TCT | GTT | GAT | GTG | 480 |
| Pro | Tyr | Lys | Glu | Lys | Pro | Ile | Gln | Asn | Gln | Ala | Lys | Ser | Val | Asp | Val | |
| 145 | | | | | 150 | | | | | 155 | | | | | 160 | |
| GAA | TAT | ACT | GTA | CAG | TTT | ACT | CCC | TTA | AAC | CCT | GAT | GAC | GAT | TTC | AGA | 528 |
| Glu | Tyr | Thr | Val | Gln | Phe | Thr | Pro | Leu | Asn | Pro | Asp | Asp | Asp | Phe | Arg | |
| | | | | 165 | | | | | 170 | | | | | 175 | | |
| CCA | GGT | CTC | AAA | GAT | ACT | AAG | CTA | TTG | AAA | ACA | CTA | GCT | ATC | GGT | GAC | 576 |
| Pro | Gly | Leu | Lys | Asp | Thr | Lys | Leu | Leu | Lys | Thr | Leu | Ala | Ile | Gly | Asp | |
| | | | 180 | | | | | 185 | | | | | 190 | | | |
| ACC | ATC | ACA | TCT | CAA | GAA | TTA | CTA | GCT | CAA | GCA | CAA | AGC | ATT | TTA | AAC | 624 |
| Thr | Ile | Thr | Ser | Gln | Glu | Leu | Leu | Ala | Gln | Ala | Gln | Ser | Ile | Leu | Asn | |
| | | 195 | | | | | 200 | | | | | 205 | | | | |
| AAA | ACC | CAC | CCA | GGC | TAT | ACG | ATT | TAT | GAA | CGT | GAC | TCC | TCA | ATC | GTC | 672 |
| Lys | Thr | His | Pro | Gly | Tyr | Thr | Ile | Tyr | Glu | Arg | Asp | Ser | Ser | Ile | Val | |
| | 210 | | | | | 215 | | | | | 220 | | | | | |
| ACT | CAT | GAC | AAT | GAC | ATT | TTC | CGT | ACG | ATT | TTA | CCA | ATG | GAT | CAA | GAG | 720 |
| Thr | His | Asp | Asn | Asp | Ile | Phe | Arg | Thr | Ile | Leu | Pro | Met | Asp | Gln | Glu | |
| 225 | | | | | 230 | | | | | 235 | | | | | 240 | |
| TTT | ACT | TAC | CAT | GTC | AAA | AAT | CGG | GAA | CAA | GCT | TAT | GAG | ATC | AAT | AAA | 768 |
| Phe | Thr | Tyr | His | Val | Lys | Asn | Arg | Glu | Gln | Ala | Tyr | Glu | Ile | Asn | Lys | |
| | | | | 245 | | | | | 250 | | | | | 255 | | |
| AAA | TCT | GGT | CTG | AAT | GAA | GAA | ATA | AAC | AAC | ACT | GAC | CTG | ATC | TCT | GAG | 816 |
| Lys | Ser | Gly | Leu | Asn | Glu | Glu | Ile | Asn | Asn | Thr | Asp | Leu | Ile | Ser | Glu | |
| | | | 260 | | | | | 265 | | | | | 270 | | | |
| AAA | TAT | TAC | GTC | CTT | AAA | AAA | GGG | GAA | AAG | CCG | TAT | GAT | CCC | TTT | GAT | 864 |
| Lys | Tyr | Tyr | Val | Leu | Lys | Lys | Gly | Glu | Lys | Pro | Tyr | Asp | Pro | Phe | Asp | |
| | | 275 | | | | | 280 | | | | | 285 | | | | |
| CGC | AGT | CAC | TTG | AAA | CTG | TTC | ACC | ATC | AAA | TAC | GTT | GAT | GTC | AAC | ACC | 912 |
| Arg | Ser | His | Leu | Lys | Leu | Phe | Thr | Ile | Lys | Tyr | Val | Asp | Val | Asn | Thr | |
| | 290 | | | | | 295 | | | | | 300 | | | | | |
| AAC | GAA | TTG | CTA | AAA | AGC | GAG | CAG | CTC | TTA | ACA | GCT | AGC | GAA | CGT | AAC | 960 |
| Asn | Glu | Leu | Leu | Lys | Ser | Glu | Gln | Leu | Leu | Thr | Ala | Ser | Glu | Arg | Asn | |
| 305 | | | | | 310 | | | | | 315 | | | | | 320 | |
| TTA | GAC | TTC | AGA | GAT | TTA | TAC | GAT | CCT | CGT | GAT | AAG | GCT | AAA | CTA | CTC | 1008 |
| Leu | Asp | Phe | Arg | Asp | Leu | Tyr | Asp | Pro | Arg | Asp | Lys | Ala | Lys | Leu | Leu | |
| | | | | 325 | | | | | 330 | | | | | 335 | | |
| TAC | AAC | AAT | CTC | GAT | GCT | TTT | GGT | ATT | ATG | GAC | TAT | ACC | TTA | ACT | GGA | 1056 |
| Tyr | Asn | Asn | Leu | Asp | Ala | Phe | Gly | Ile | Met | Asp | Tyr | Thr | Leu | Thr | Gly | |
| | | | 340 | | | | | 345 | | | | | 350 | | | |
| AAA | GTA | GAG | GAT | AAT | CAC | GAT | GAC | ACC | AAC | CGT | ATC | ATA | ACC | GTT | TAT | 1104 |

| | | | | | | | | | | | | | | |
|---|---|---|---|---|---|---|---|---|---|---|---|---|---|---|
| Lys | Val | Glu | Asp | Asn | His | Asp | Asp | Thr | Asn | Arg | Ile | Ile | Thr | Val | Tyr |
| | | 355 | | | | 360 | | | | | 365 | | | | |

| ATG | GGC | AAG | CGA | CCC | GAA | GGA | GAG | AAT | GCT | AGC | TAT | CAT | TTA | GCC | TAT | 1152 |
|---|---|---|---|---|---|---|---|---|---|---|---|---|---|---|---|---|
| Met | Gly | Lys | Arg | Pro | Glu | Gly | Glu | Asn | Ala | Ser | Tyr | His | Leu | Ala | Tyr | |
| | 370 | | | | | 375 | | | | | 380 | | | | | |

| GAT | AAA | GAT | CGT | TAT | ACC | GAA | GAA | GAA | CGA | GAA | GTT | TAC | AGC | TAC | CTG | 1200 |
|---|---|---|---|---|---|---|---|---|---|---|---|---|---|---|---|---|
| Asp | Lys | Asp | Arg | Tyr | Thr | Glu | Glu | Glu | Arg | Glu | Val | Tyr | Ser | Tyr | Leu | |
| 385 | | | | | 390 | | | | | 395 | | | | | 400 | |

| CGT | TAT | ACA | GGG | ACA | CCT | ATA | CCT | GAT | AAC | CCT | AAC | GAC | AAA | TAA | 1245 |
|---|---|---|---|---|---|---|---|---|---|---|---|---|---|---|---|
| Arg | Tyr | Thr | Gly | Thr | Pro | Ile | Pro | Asp | Asn | Pro | Asn | Asp | Lys | | |
| | | | | 405 | | | | | 410 | | | | | | |

( 2 ) INFORMATION FOR SEQ ID NO: 2:

( i ) SEQUENCE CHARACTERISTICS:
        ( A ) LENGTH:26 bases
        ( B ) TYPE:nucleotide
        ( C ) STRANDEDNESS:single
        ( D ) TOPOLOGY:linear ( x i ) SEQUENCE DESCRIPTION: SEQ ID NO:2:

TGGAATTCAT GAAAAATTAC TTATCT 26

( 2 ) INFORMATION FOR SEQ ID NO: 3:

( i ) SEQUENCE CHARACTERISTICS:
        ( A ) LENGTH:28 bases
        ( B ) TYPE:nucleotide
        ( C ) STRANDEDNESS:single
        ( D ) TOPOLOGY:linear ( x i ) SEQUENCE DESCRIPTION: SEQ ID NO:3:

TGGATCCTTA TTTGTCGTTA GGGTTATC 28

( 2 ) INFORMATION FOR SEQ ID NO: 4:

( i ) SEQUENCE CHARACTERISTICS:
        ( A ) LENGTH:31 bases
        ( B ) TYPE:nucleotide
        ( C ) STRANDEDNESS:single
        ( D ) TOPOLOGY:linear ( x i ) SEQUENCE DESCRIPTION: SEQ ID NO:4:

GGAATTCATG ATTGCTGGAC CTGAGTGGCT G 31

( 2 ) INFORMATION FOR SEQ ID NO: 5:

( i ) SEQUENCE CHARACTERISTICS:
        ( A ) LENGTH:17 bases
        ( B ) TYPE:nucleotide
        ( C ) STRANDEDNESS:single
        ( D ) TOPOLOGY:linear ( x i ) SEQUENCE DESCRIPTION: SEQ ID NO:5:

ATCATCGAAC TAGTTAA 17

( 2 ) INFORMATION FOR SEQ ID NO: 6:

( i ) SEQUENCE CHARACTERISTICS:
        ( A ) LENGTH:17 bases
        ( B ) TYPE:nucleotide
        ( C ) STRANDEDNESS:single
        ( D ) TOPOLOGY:linear ( x i ) SEQUENCE DESCRIPTION: SEQ ID NO:6:

GAATCAAGAC ATTAGTC 17

( 2 ) INFORMATION FOR SEQ ID NO: 7:

( i ) SEQUENCE CHARACTERISTICS:
( A ) LENGTH:15 bases
( B ) TYPE:nucleotide
( C ) STRANDEDNESS:single
( D ) TOPOLOGY:linear ( x i ) SEQUENCE DESCRIPTION: SEQ ID NO:7:

GTGGCGCGAT GCCAC 15

( 2 ) INFORMATION FOR SEQ ID NO: 8:

( i ) SEQUENCE CHARACTERISTICS:
( A ) LENGTH:17 bases
( B ) TYPE:nucleotide
( C ) STRANDEDNESS:single
( D ) TOPOLOGY:linear ( x i ) SEQUENCE DESCRIPTION: SEQ ID NO:8:

GCAACCATTA CTGATCG 17

( 2 ) INFORMATION FOR SEQ ID NO: 9:

( i ) SEQUENCE CHARACTERISTICS:
( A ) LENGTH:17 bases
( B ) TYPE:nucleotide
( C ) STRANDEDNESS:single
( D ) TOPOLOGY:linear ( x i ) SEQUENCE DESCRIPTION: SEQ ID NO:9:

CCAGTACAAA ATCAAGC 17

( 2 ) INFORMATION FOR SEQ ID NO: 10:

( i ) SEQUENCE CHARACTERISTICS:
( A ) LENGTH:17 bases
( B ) TYPE:nucleotide
( C ) STRANDEDNESS:single
( D ) TOPOLOGY:linear ( x i ) SEQUENCE DESCRIPTION: SEQ ID NO:10:

CTAGCTATCG GTGACAC 17

( 2 ) INFORMATION FOR SEQ ID NO: 11:

( i ) SEQUENCE CHARACTERISTICS:
( A ) LENGTH:15 bases
( B ) TYPE:nucleotide
( C ) STRANDEDNESS:single
( D ) TOPOLOGY:linear ( x i ) SEQUENCE DESCRIPTION: SEQ ID NO:11:

CAGAGATCAG GTCAG 15

( 2 ) INFORMATION FOR SEQ ID NO: 12:

( i ) SEQUENCE CHARACTERISTICS:
( A ) LENGTH:16 bases
( B ) TYPE:nucleotide
( C ) STRANDEDNESS:single
( D ) TOPOLOGY:linear ( x i ) SEQUENCE DESCRIPTION: SEQ ID NO:12:

GTTAAGAGCT GCTCGC 16

( 2 ) INFORMATION FOR SEQ ID NO: 13:

( i ) SEQUENCE CHARACTERISTICS:
( A ) LENGTH:17 bases
( B ) TYPE:nucleotide (C) STRANDEDNESS:single
(D) TOPOLOGY:linear (xi) SEQUENCE DESCRIPTION: SEQ ID NO:13:

CCAGTTAAGG TATAGTC 17

(2) INFORMATION FOR SEQ ID NO: 14:

(i) SEQUENCE CHARACTERISTICS:
(A) LENGTH:16 bases
(B) TYPE:nucleotide
(C) STRANDEDNESS:single
(D) TOPOLOGY:linear (xi) SEQUENCE DESCRIPTION: SEQ ID NO:14:

TCTCGTTCTT CTTCGG 16

METHOD FOR THE ISOLATION AND EXPRESSION OF A GENE WHICH CODES FOR STREPTOKINASE, NUCLEOTIDE SEQUENCE OBTAINED, RECOMBINANT DNA AND TRANSFORMED MICROORGNAISMS

The present invention relates to the field of biotechnology and genetic engineering techniques and in particular a method for the isolation and cloning of a novel nucleotide sequence which codes for a streptokinase, as well as the recombinant DNA obtained therefrom which is used for the transformation of different host organisms.

Streptokinases are plasminogen activators from prokaryotic cells, which are usually secreted into the culture medium by a large number of haemolytic Streptococci of different serotypes. Being proteins of bacterial origin, some antigenic responses to them have been detected (Dykewies, M.S. et al., 1985 and McGroth, K.G. et al., 1985). Their molecular weight is approximately 47,000 dalton.

The function in the pathogenicity of Streptococci is not known exactly, although potentially it must contribute to elimination or avoidance of the formation of fibrin barriers around the infection.

During interaction of streptokinase with the plasminogen which is in human plasma, it was found that the protein is capable of converting the latter to plasmin, which displays proteolytic activity and can degrade fibrin clots into soluble products.

Streptokinase, urokinase and tissue-type plasminogen activator are at present used as thrombolytic agents in the treatment of disorders which collectively represent one of the greatest causes of death in the world, such as myocardial infarct, pulmonary, arterial or venous thromboembolism, surgical complications and other cases of thrombosis.

There are physicochemical and immunological differences and differences in respect of substrate specificity which bear witness to molecular heterogeneity of streptokinases of different origins, although they are all closely related in respect of function.

Combined with the low yields obtained in production of the protein and the pathogenicity of its natural host, the Streptococcus strains used for the industrial production of streptokinase secrete other products into the culture medium, such as deoxyribonucleases, streptolysin or hyaluronidase and proteases, which makes the process of purifying the desired protein difficult. On the other hand, it has not yet been possible to obtain genetically improved strains from these hosts due to the lack of a developed methodology for the gene transfer.

It is due to these drawbacks that the cloning of different isolated genes which code for these proteins has been attempted, using prokaryotic and eukaryotic hosts.

The German Democratic Republic patent no. 249493, IPC: C12 N 15/00, describes the cloning and expression of a gene which codes for streptokinase from strain H46A of *Streptococcus equisimilis*, belonging to *Streptococcus* type C, using *E. coli* bacteria as the host, wherein levels of excretion into the medium from 0.1 to 1.8 mg/1 are obtained, depending on the age of the culture.

The coding sequence for this gene, which was called SKC, was subsequently determined, including its signal peptide, as well as the identification of the primary structure of adjacent regions involved in the control of transcription and translation of said gene (Malke, H. et al., 1985).

Other nucleotide sequences of genes which code for streptokinases from Streptococcus types G and A have been characterised (Water, F. et al., 1989). In particular, the gene which determines streptokinase type A (gene SKA) from strain 49 type M of *Streptococcus piogenes* was cloned and expressed in strain JM109 of *E. coli* and in *Streptococcus sanguis* Challis 57E (Huang, T.T. et al., 1989). In both cases, protein levels of 0.64 mg/1 and 40 μg/1 respectively were produced. In the case of *E. coli*, 94% of the protein recovered was in the periplasmic space and 6% in the cytosol, whereas in *S. sanguis* all the enzyme was found extracellularly. Moreover, many clones producing streptokinase in *E. coli* were very unstable, as in some cases the SKA gene was deleted or the host cells died owing to some lethal activity of the gene product in question.

In the case of *S. sanguis*, the protein molecule obtained was approximately 3,000 dalton less than native streptokinase and the absence of 32 amino acids from the C-terminal end was detected; however, biological activity was not affected (Huang, T.T. et al., 1989).

Subsequently, conclusive results were obtained with respect to the difficulty of cloning and expressing the isolated SKC gene in *E. coli*, it being found that the gene product interferes with the normal physiology of the host, which is shown by the mucosity of the cells which carry this gene, by the incomplete export of streptokinase into the periplasmic space, by the structural instability of the plasmids which carry the SKC gene and which are designated for the expression of high levels of the protein, as well as by the drawbacks encountered in cloning streptokinase genes from additional serotypes of Streptococcus in plasmids of *E. coli* and unsuccessful attempts to express heterologous genes under the control of expression-excretion signals of the SKC gene itself (Muller, J. et al., 1989).

More recently the company Phillips Petroleum (patent DD257646, IPC: C 12 N 15/00, and Haggenson, M.J. et al., 1989) has obtained the expression of streptokinase in the methylotrophic yeast *Pichia pastoris*, under the control of gene regulatory sequences of alcohol oxidase, wherein yields of the desired product using continuous fermentation of the order of 77-250 mg/1 culture medium were obtained, with an intermediary cell density of 46 g/1. This system uses the SKC gene, contained in the plasmid pMF5 which is licensed to this company by Dr. J.J Ferretti of Oklahoma University, USA, in the expression vectors.

The controllability of the system makes it attractive, taking into account that it can easily be repressed by using glucose or glycerol and induced with methanol; nevertheless, its application is limited to this host.

It is the object of the present invention to obtain high levels of streptokinase yield in different host systems, by the use of expression vectors which carry a novel nucleotide sequence which represents a genetic variant not described before and which codes for a bioactive streptokinase, which contains the active portion corresponding to streptokinase from *Streptococcus equisimilis* of type C, strain ATCC-9542. The novel isolated gene is called SKC-2, and codes for a protein of the same molecular weight as the one encoded by SKC; it has the fundamental characteristic of stability in vectors of *E. coli* and yeasts, adverse effects on cells growth or viability not being found in a single case, which makes it possible to obtain yields greater than those reported up to now in both hosts, in respect of the product obtained, which indicates a streptokinase different to those known up to now, with the desired biological activity.

The present invention relates to a method for the isolation and expression of a novel nucleotide sequence corresponding to the SKC-2 gene, the product of which is a protein of approximately 47,000 dalton. Said protein belongs to the streptokinases, which are distinguished by their fibrinolytic activity.

The present invention also relates to this gene, the sequence of which corresponds to seq. id. No. 1 in the Sequence Listing.

It was obtained from the genome of the *Streptococcus equisimilis* type C strain (ATCC-9542) by gene amplification using the polymerase chain reaction (PCR) from three synthetic oligonucleotides called SK1, SK2 and SK3 having the sequences:

| | |
|---|---|
| SK1 5'... TGGAATTCATGAAAAATTACTTATCT... 3' | seq. id. No. 2 |
| SK2 5'... TGGATCCTTATTTGTCGTTAGGGTTATC... 3' | seq. id. No. 3 |
| SK3 5'... GGAATTCATGATTGCTGGACCTGAGTGGCTG... 3' | seq. id. No. 4 | and constitute a novel aspect for this method. These primers further carry restriction sites which are not found in the gene and which allow direct cloning in an expression vector. On the other hand, the SK2 which hybridises at the 5' end carries an ATG which acts as a site for initiating translation and removes the signal peptide of SKC-2. The three oligonucleotides were synthesised from the SKC sequences published by Malke et al., 1985; and with them were marked the boundaries of the exact fragment of the gene which codes for the mature protein or the complete gene including the signal peptide.

Another novel aspect of this method is the possibility of expressing the isolated gene in both bacteria and yeasts, high levels of expression being achieved in both cases.

Figure 3:
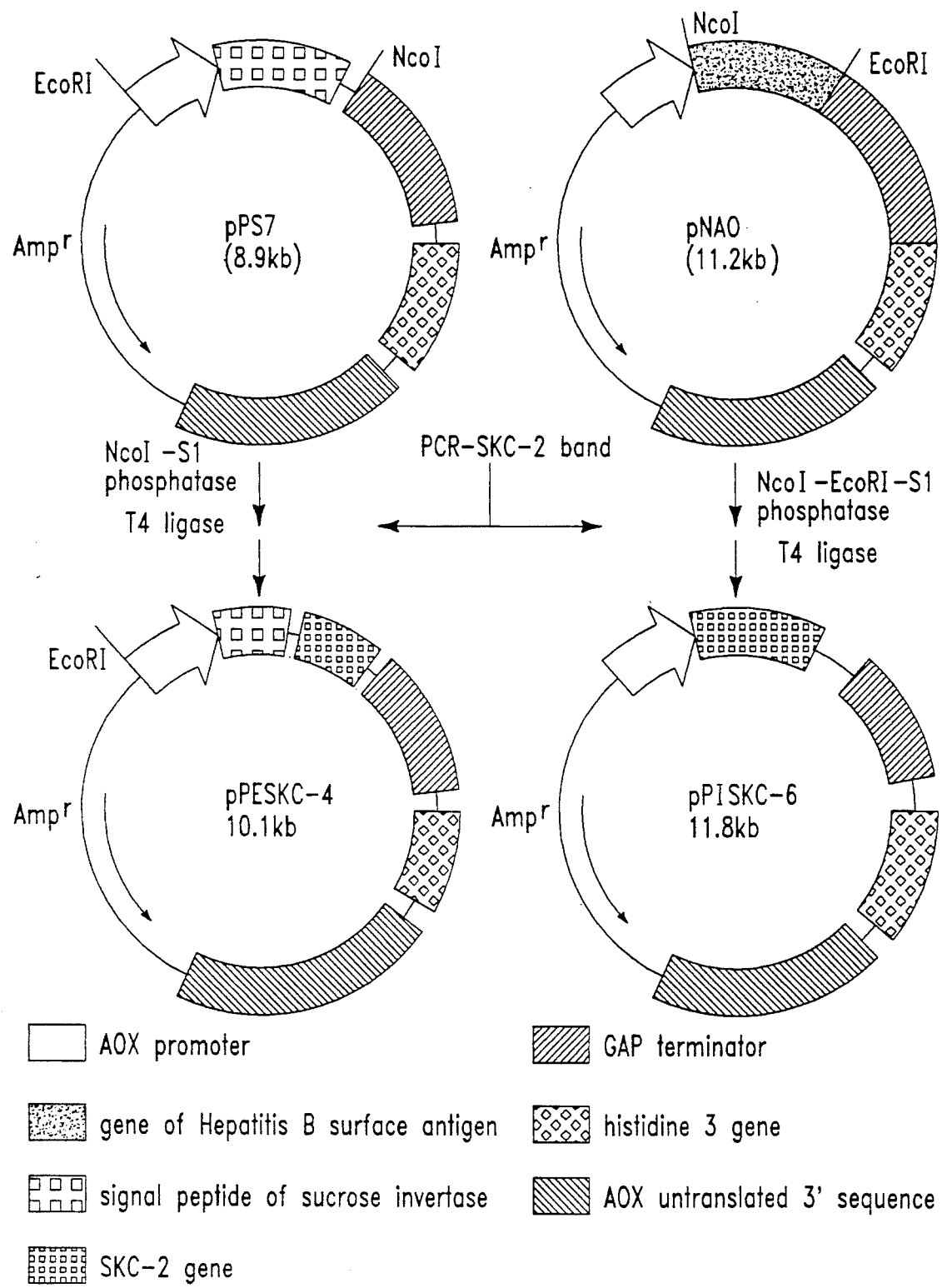

The present invention also relates to recombinant DNA which includes the SKC-2 gene, such as vectors for the expression of this gene, in bacteria pEKG3 (FIG. 1), and in yeasts pPESKC-4 and pPISKC-6 (FIG. 3). In particular for expression in *E. coli*, the SKC-2 gene with or without its signal peptide is cloned under the tryptophan promoter and with the transcription termination signal of phage T4. For yeasts there was used the expression vector referred to in the Inventor's Certificate application number 7/90 (Cu), in which the SKC-2 gene is located behind the signal peptide of sucrose invertase (SUC2) controlled by the alcohol oxidase gene promoter (AOX1) of *Pichia pastoris* and which carries the termination signal of the glyceraldehyde-3-phosphate dehydrogenase (GAPt) gene of *Saccharomyces cerevisiae* for the extracellular expression variant, this vector being called pPESKC-4. For the intracellular expression of SKC-2, the vector pPISKC-6 is used which does not contain the signal peptide of SUC-2 behind the AOX1 promoter, and this is obtained by inserting the SKC-2 gene in the expression vector pNAO (kindly provided by Muzio, CIGB, Havana, Cuba) (FIG. 3). The HIS3 gene of *S. cerevisiae* is used as a selection marker in both vectors, and the expression cassette referred to above is flanked by 5' and 3' sequences of the AOX gene of *Pichia pastoris* for integration.

The present invention also relates to the microorganisms resulting from transformation of *E. coli* strain W3110 with vector pEKG3, and of mutant MP-36 of *Pichia pastoris* referred to in Inventor's Certificate application 7/90 with expression vectors pPESKC-4 and pPISKC-6, which are characterised as expressing high levels of streptokinase, and having good viability (the product has no adverse effects on cell growth) and high stability of the strains transformed.

The transformed *E. coli* clone was called HSK-M and exhibits levels of expression of the product of the SKC-2 gene greater than 350 mg/l culture medium.

The transformed *Pichia pastoris* strains MSK-M4 and MSK-M6 produce streptokinase levels intracellularly and extracellularly respectively which vary between 1.0 and 1.2 g/l culture medium.

The method described in the present invention, given the levels of expression never before reported for this product, makes it possible to reach optimum purity thereof for its administration to human beings and animals, without the need to develop a complex and costly process for purification.

EXAMPLES

The following examples are intended to illustrate but not limit the invention. *E. coli* and *Pichia pastoris* are used as host systems in these examples; nevertheless, other eukaryotic and prokaryotic cells can be used for the method described in the present invention.

EXAMPLE 1

For the isolation of genomic DNA of *Streptococcus equisimilis* of type C, strain ATCC-9542 was used as a source thereof for cloning the SK gene. The cells of *Streptococcus equisimilis* were grown in Brain Heart Infusion Medium (GIBCO) at 240 r.p.m. for 12 hours at 37° C. in 5-ml pre-cultures acting as an inoculum which was grown for 12 hours in a 300-ml Erlenmeyer flask. The cells were collected by centrifugation at 3,000 r.p.m. and resuspended in 8 ml lyse (4.5 g glucose, 1.86 g EDTA, 1.51 g tris-HCl, in 500 ml sterile water, pH=8), 80 μl of lysozyme were added at a concentration of 10 mg/ml, and the suspension was incubated for 30 minutes at 37° C. Next, to obtain efficient cell rupture, 500 μl pronase (Boehringer), 1 ml SDS at 10% and 200 μl EDTA, 0,5 M, pH=8, were added and the suspension was incubated for 2 hours at 50° C. with smooth agitation. Successive treatments with phenol, phenol-chloroform and chloroform were carried out, and the genomic DNA was precipitated with absolute ethanol and NH$_4$Ac,, 7.5 M.

The yield obtained was 100 μg per 300-ml Erlenmeyer culture flask. The presence of the gene which codes for streptokinase was verified by the Southern blot technique (Maniatis et al., 1982).

EXAMPLE 2

For subcloning in bacteria, 1 μg genomic DNA of the *Streptococcus equisimilis* type C strain (ATCC-9542) was taken and the gene which codes for SKC-2 was amplified by a PCR (Randall et al., 1988) using the oligonucleotides SK1 and SK2 for cloning the gene with its signal peptide and SK2-SK3 for cloning without it.

In each reaction 100 pmol of each oligonucleotide, 2 units of Taq polymerase (Perkin Elmer, USA) and 200

µmol of each dNTP were used and the reactions were performed in 10 mM MgCl$_2$, 100 mM dTT, 10 mM NaCl and 100 µg/ml gelatine.

Thirty amplification cycles were performed, wherein in each one the reaction was incubated at 95° C. for 1 minute for denaturisation, at 52° C. for 45 seconds for hybridisation of the oligonucleotides and at 70° C. for 80 seconds for extension. An efficiency greater than 5% of amplification was obtained.

For cloning in bacteria (*E. coli*), a genetic construct different from those reported for the expression of this product was used, wherein the tryptophan promoter of *E. coli* and the termination signal of bacteriophage T4 are used. The fragments amplified in the PCR were digested with BamHI and ligated with the vector ptrip-NcoI-S1-BamHI (Estrada et al., 1988). This construct was transformed into a preparation of competent cells prepared according to Dagert et al. (1974) and Hanahan et al. (1983), of *E. coli* strain HB101 {(r$_B^-$m$_B^-$), supE$^{44}$, ara-14, galK-2, lacY1, proA2, rpsL20, (Str$^R$), xyl-5, mtl-5, mtl-1, recA13}, which had a frequency greater than 10$^7$ transformants per g DNA.

The colonies obtained were applied to plates of LB medium (10 g/l trypton, 5 g/l yeast extract, 10 g/l sodium chloride) and 50 µg/ml ampicillin, and hybridised according to Maniatis et al. (1982), using as a probe the fragment resulting from the amplification in the PCR, which was marked using dATP$^{32}$ (Amersham, UK) and the Klenow fragment of DNA-polymerase I of *E. coli* (Maniatis et al., 1982) in Whatman 541 filters for 30 minutes at 37° C., the reaction being terminated by EDTA and heat. 4% of the colonies were positive clones, which were examined by restriction analysis and had the same pattern of digestion with more than 10 restriction enzymes; moreover the positive clones were checked by double chain DNA sequencing (Sanger et al., 1977), using therefor an oligonucleotide of 17 bases (5'...ATCATCGAACTAGT-TAA...3', seq. id. No. 5) which hybridises at the 3' end of the promoter, with which it was corroborated that joining of the latter to the SKC-2 gene was as desired.

The selected clone was called pEKG-3 (FIG. 1), which was subjected to fermentation to realise the characterisation of the product.

The plasmid of clone pEKG3 was purified using a CsCl gradient and the sequences of the SKC-2 gene were established, each time using 2 g of plasmid, and using the oligonucleotides which appear below as primers:

| | |
|---|---|
| SSK-01 5'... GAATCAAGACATTAGTC... 3' | seq. id. No. 6 |
| SSK-02 5'... GTGGCGCGATGCCAC... 3' | seq. id. No. 7 |
| SSK-03 5'... GCAACCATTACTGATCG... 3' | seq. id. No. 8 |
| SSK-04 5'... CCAGTACAAAATCAAGC... 3' | seq. id. No. 9 |
| SSK-05 5'... CTAGCTATCGGTGACAC... 3' | seq. id. No. 10 |
| SSK-06 5'... CAGAGATCAGGTCAG... 3' | seq. id. No. 11 |
| SSK-07 5'... GTTAAGAGCTGCTCGC... 3' | seq. id. No. 12 |
| SSK-08 5'... CCAGTTAAGGTATAGTC... 3' | seq. id. No. 13 |
| SSK-09 5'... TCTCGTTCTTCTTCGG... 3' | seq. id. No. 14 |

The protocol followed was basically according to Sanger et al. (1977), and dATP$^{32}$ and S$^{35}$dATP (Amersham, UK) were used.

FIG. 2 shows a comparison between the amino acid sequence derived from the base sequence of SKC-2, and those of the genes SKC (Malke et al., 1986), SKA and SKG (Water, F. et al., 1989).

The plasmid pEKG3 was transformed in several *E. coli* strains such as W-3110, JM-101, LE392 and MC-1061 and the expression of streptokinase was compared between them. The best results were obtained with strain W3110 (F$^-$supF supE hsdR galK TrpR metB lacY tonA), owing to which it was selected to be subjected to fermentation, wherein stable expression levels greater than 20% of the total protein content of the cells were obtained, and 350-400 mg streptokinase per litre of culture medium were obtained.

EXAMPLE 3

For subcloning of the SKC-2 gene in yeast, strain MP36 of *Pichia pastoris* was used as the host, and variants were made for intracellular and extracellular expression from the plasmids pNAO and pPS7 (FIG. 3), using the signal peptide of sucrose invertase for the extracellular construct, and in both cases subcloning the gene under the control of the alcohol oxidase (AOX) promoter, using as the terminator at the 3' end the termination signal of the glyceraldehyde-3-phosphate dehydrogenase gene of *S. cerevisiae* and a non-coding 3' region of the AOX gene for integration by homology in the genome of the yeast, further relying on the gene encoding histidine 3, which was used for selection in strain MP36 his$^-$.

The vector pPESKC4 (plasmid for extracellular expression of the protein) was obtained from the vector construct pPS7-NcoI-S1 nuclease-phosphatase ligated with the SKC-2 gene amplified by PCR from pEKG3 with the oligonucleotide SK2 and a new primer which hybridises with the 5' end of the gene and eliminates the ATG which had been inserted for expression in bacteria. In the case of intracellular expression, pPISKC6 was obtained (plasmid for intracellular expression of the protein) from the vector pNAO-NcoI-EcoRI-S1 nuclease-phosphatase ligated with the band of SKC-2 amplified by PCR, with the primers SK2 and SK3 with which is obtained the exact gene which codes for streptokinase with an ATG at its 5' end (FIG. 3). Both plasmids were transformed in strain MP36 his$^-$, using the protocol according to Cregg, J. et al. (1985).

The positive clones were studied by the Southern blot method (Maniatis et al., 1982), and out of those which had the correct integration were selected the most productive in each case for characterisation of the product.

The expression of recombinant streptokinase obtained in *P. pastoris* extracellularly was 1-1.2 g/l culture supernatant, and in case of the intracellular construct more than 1.0 g/l culture.

In the construct for extracellular expression, the glycosylated protein was obtained with a molecular weight greater than 67,000 dalton, it being corroborated by Western blotting that it decreases to the molecular weight of native streptokinase when it is digested with endoglycosidase H. This was carried out by taking a portion having a concentration equal to 1 mg/ml in a sodium citrate solution, 0.05 molar, pH=5.5, and denaturing it by the addition of SDS (final concentration 0.02%) and heating at 100° C. for 10 minutes, then leaving it to cool to ambient temperature and adding 20 milliunits (mU) of endoglycosidase H (endo H) and leaving it for 16 hours at 37° C., at the end of which it is subjected to subsequent heating at 100° C. for 5 minutes and 10 mU of endo H are added, followed by 12 hours' incubation at 37° C., and it is applied to a 12.5% polyacrylamide gel and compared with an undeglycosylated sample.

The streptokinase produced in *Pichia pastoris* in both constructs maintains biological activity, not varying its affinity for plasminogen and being in fact another variant for the use of this protein in clinical medicine.

EXAMPLE 4

To verify the biological activity of the product of the SKC-2 gene, the pure recombinant streptokinase obtained from both bacteria and yeast was used for acute and subacute toxicology tests on rats, wherein satisfactory and acceptable results were obtained to allow its use in human and animal therapeutics. Its in vivo fibrinolytic activity was verified in clinical tests on animals, wherein there was success in dissolving clots in the coronary and femoral arteries of dogs, blood parameters being maintained similar to those reported in the literature with this type of product.

The product of the SKC-2 gene showed a specific activity of 50,000–100,000 IU/mg, which was measured on plates of agarose-fibrin (Astrup et al., 1952), chromogenic substrate (Friberger et al., 1982) and in vitro clot lysis according to Westlund et al. (1985).

EXAMPLE 5

To verify the amino acid sequence derived from the base sequence of the SKC-2 gene, an analysis was made of the pure product by high-performance liquid chromatography in reverse phase (HPLC-RP), using therefor a C8 4.6×250 mm column (Baker, USA), wherein there was used the gradient 5 minutes at 0% buffer B and up to 90% B in 55 minutes, with buffer A (trifluoroacetic acid (TFA, Pierce, USA) at 0.1% in distilled water) and buffer B (TFA at 0.5% in acetonitrile (Lichrosolv, Merck, FRG)), maintaining a flow rate of 0.8 ml/min.

With the protein with a high degree of purity, the amino acid sequence derived from the base sequence obtained from the SKC-2 gene was verified by sequencing it by mass spectrometry For this the protein was digested with different enzymes and with combinations of them. The enzymes used were chymotrypsin, endoproteinase Glu-C, endoproteinase Lys-C and trypsin.

From the analysis of the mass spectra of the peptides obtained in each of the digestions with the different enzymes, the map of the amino acid sequence of the protein was constructed by superposition, which made it possible to verify that there is in this case 100% correspondence between the sequence of the SKC-2 gene and the amino acid sequence of the protein obtained.

The *E. coli* HSK-M [pEKG3] strain, based on the *E. coli* strain W3110 and containing the plasmid pEKG3, was deposited on June 11, 1990, with the Centraalbureau voor Schimmelcultures (CBS), Baarn, The Netherlands, and obtained deposit number CBS 243.90.

Likewise, the *Pichia pastoris* MSK-M4 [pPESKC-4] strain, based on the *Pichia pastoris* strain MP-36 and containing the plasmid pPESKC-4, was deposited on June 11, 1990, with the Centraalbureau voor Schimmelcultures (CBS), Baarn, The Netherlands, and obtained deposit number CBS 244.90.

---

We claim:

1. A method for producing streptokinase by expression of a gene encoding said streptokinase which comprises the steps of transforming a host cell with an expression vector containing a streptokinase gene (skc-2) consisting essentially of the nucleotide sequence SEQ ID NO: 1 in the Sequence Listing operably linked to an effective promoter and transcription terminator, growing said transformed host cell and isolating the streptokinase so produced.

2. The method of claim 1 wherein said host cell is a bacterium.

3. The method of claim 2 wherein said bacterium is *Escherichia coli*.

4. The method of claim 2 wherein said bacterium is *Escherichia coli* strain W3110.

5. The method of claim 2 wherein said expression vector is a plasmid containing the skc-2 gene operably linked to the *Escherichia coli* tryptophan promoter and the T4 transcription terminator.

6. The method of claim 5 wherein said expression vector is the plasmid pEKG3 contained in *Escherichia coli* strain CBS 243.90.

7. The method of claim 1 wherein said host cell is a yeast.

8. The method of claim 7 wherein said yeast is *Pichia pastoris*.

9. The method of claim 7 wherein said yeast is *Pichia pastoris* his3 strain MP-36.

10. The method of claim 7 wherein said expression vector is a plasmid containing the skc-2 gene operably linked to the *Pichia pastoris* alcohol oxidase promoter (AOXI) and the *Saccharomyces cerevisiae* glyceraldehyde-3-phosphate dehydrogenase termination sequence (GAPt).

11. The method of claim 10 wherein said expression vector contains the *Saccharomyces cerevisiae* his3 gene as a selection marker.

12. The method of claim 11 wherein said expression vector is the plasmid pPESKC-4 contained in *Pichia pastoris* strain CBS 244.90.

13. An isolated and purified nucleic acid consisting essentially of the nucleotide sequence SEQ ID NO:1 in the Sequence Listing.

14. An expression vector for the expression of streptokinase in a host cell, said vector containing a streptokinase gene (skc-2) consisting essentially of the nucleotide sequence SEQ ID NO: 1 in the Sequence Listing operably linked to an effective promoter and transcription terminator.

15. The expression vector of claim 14 containing the skc-2 gene operably linked to the *Escherichia coli* tryptophan promoter and the T4 transcription terminator for expression of said skc-2 gene in bacteria.

16. The expression vector of claim 15 which is the plasmid pEKG3 contained in *Escherichia coli* strain CBS 243.90.

17. The expression vector of claim 14 containing the skc-2 gene operably linked to the *Pichia pastoris* alcohol oxidase promoter (AOXI) and the *Saccharomyces cerevisiae* glyceraldehyde-3 phosphate dehydrogenase termination sequence (GAPt) for expression of said skc-2 gene in yeast.

18. The expression vector of claim 17 containing the *Saccharomyces cerevisiae* his3 gene as a selection marker 19. The expression vector of claim 18 which is the plasmid pPESKC-4 and pPISKC-6.

20. A host cell for producing streptokinase by expression of a gene encoding said streptokinase, said host cell being transformed with an expression vector containing a streptokinase gene (skc-2) consisting essentially of the nucleotide sequence SEQ ID NO:1 in the Sequence Listing operably linked to an effective promoter and transcription terminator.

21. The host cell of claim 20 which is a bacterium.

22. The host cell of claim 20 which is *Escherichia coli*.

23. The host cell of claim 20 which is *Escherichia coli* strain W3110.

24. The host cell of claim 20 which is a yeast.

25. The host cell of claim 20 which is *Pichia pastoris*.

26. The host cell of claim 20 which is *Pichia pastoris* his3 strain MP-36.

* * * * *